(12) United States Patent
Ueda et al.

(10) Patent No.: US 11,286,481 B2
(45) Date of Patent: Mar. 29, 2022

(54) METHOD FOR PRODUCING COMPLEX OF RNA MOLECULE AND PEPTIDE, AND UTILIZATION THEREOF

(71) Applicant: CUBICStars, Inc., Fukuoka (JP)

(72) Inventors: Hiroki Ueda, Saitama (JP); Yoshihiro Shimizu, Saitama (JP); Shoko Harada, Saitama (JP); Katsuhiko Matsumoto, Saitama (JP)

(73) Assignee: CUBICSTARS, INC., Fukuoka (JP)

( * ) Notice: Subject to any disclaimer, the term of this patent is extended or adjusted under 35 U.S.C. 154(b) by 17 days.

(21) Appl. No.: 16/494,996

(22) PCT Filed: Mar. 15, 2018

(86) PCT No.: PCT/JP2018/010223
§ 371 (c)(1),
(2) Date: Sep. 17, 2019

(87) PCT Pub. No.: WO2018/168999
PCT Pub. Date: Sep. 20, 2018

(65) Prior Publication Data
US 2020/0283761 A1    Sep. 10, 2020

(30) Foreign Application Priority Data

Mar. 17, 2017 (JP) .............................. JP2017-053621

(51) Int. Cl.
*C12N 15/11* (2006.01)
*C12N 15/10* (2006.01)

(52) U.S. Cl.
CPC .......... *C12N 15/11* (2013.01); *C12N 15/1062* (2013.01); *C12N 2310/11* (2013.01); *C12N 2310/321* (2013.01); *C12N 2310/322* (2013.01)

(58) Field of Classification Search
CPC .... C12N 15/11; C12N 15/1062; C12N 15/09; C12P 21/02; C40B 40/08
See application file for complete search history.

(56) References Cited

U.S. PATENT DOCUMENTS

| | | |
|---|---|---|
| 6,207,446 B1 | 3/2001 | Szostak et al. |
| 6,261,804 B1 | 7/2001 | Szostak et al. |
| (Continued) | | |

FOREIGN PATENT DOCUMENTS

| | | |
|---|---|---|
| JP | 2002-513281 | 5/2002 |
| JP | 2013/226138 | 11/2013 |
| (Continued) | | |

OTHER PUBLICATIONS

Reyes et al. "PURE mRNA display and cDNA display provide rapid detection of core epitope motif via high-throughput sequencing" Biotechnology and Bioengineering. 2021;118:1702-1715 (Year: 2021).*

(Continued)

*Primary Examiner* — Richard A Schnizer
*Assistant Examiner* — K. Lau
(74) *Attorney, Agent, or Firm* — Kristina Castellano; Castellano PLLC

(57) ABSTRACT

The present invention provides a method for efficiently obtaining a complex in which a gene (mRNA) and a peptide as a translation product thereof are linked via a peptide receptor molecule, and utilization thereof. In the method of the present invention, at least one 2'-modified nucleoside derivative is introduced into a 5' end side of an antisense strand of a template DNA.

8 Claims, 6 Drawing Sheets
Specification includes a Sequence Listing.

(56) References Cited

U.S. PATENT DOCUMENTS

| | | | |
|---|---|---|---|
| 2008/0058217 A1 | 3/2008 | Szostak et al. | |
| 2010/0323364 A1 | 12/2010 | Sekine et al. | |
| 2012/0208720 A1 | 8/2012 | Kashiwagi et al. | |
| 2013/0288908 A1 | 10/2013 | Fujino et al. | |
| 2013/0288930 A1 | 10/2013 | Kojoh et al. | |
| 2016/0068835 A1* | 3/2016 | Reid et al. | C12N 15/1062 |

FOREIGN PATENT DOCUMENTS

| | | |
|---|---|---|
| WO | 98/31700 A1 | 7/1998 |
| WO | 2009/099073 A1 | 8/2009 |
| WO | 2011/049157 A1 | 4/2011 |
| WO | 2012/074029 A1 | 6/2012 |

OTHER PUBLICATIONS

International Search Report for PCT/JP2018/010223, dated Jun. 12, 2018.

English Translation of International Preliminary Report on Patentability for PCT/JP2018/010223, dated Sep. 26, 2019.

Nemoto et al., "In vitro virus: Bonding of mRNA bearing puromycin at the 3'-terminal end to the C-terminal end of its encoded protein on the ribosome in vitro", FEBS Letters 414: 405-408, Jun. 30, 1997.

Roberts et al., "RNA-peptide fusions for the in vitro selection of peptides and proteins", Proc. Natl. Acad. Sci. USA, 94: 12297-12302, Nov. 1997.

Kao, C., et al., "A simple and efficient method to transcribe RNAs with reduced 3' heterogeneity", Methods, 2001, vol. 23, No. 3, pp. 201-205.

Liu, R., et al., "Optimized synthesis of RNA-protein fusions for in vitro protein selection", Meth. Enzymol., 2000, vol. 318, pp. 268-293.

Extended European Search Report (EESR) dated Nov. 23, 2020, in the corresponding EP patent application No. 18768096 2.

"mRNA display: from basic principles to macrocycle drug discovery"; Kristopher Josephson et al.; Apr. 1, 2014; Drug Discovery Today, vol. 19, No. 4, pp. 388-399, XP055333289, Amsterdam, NL ISSN: 1359-6446, DOI: 10.1016/j.drudis.2013.10.011.

* cited by examiner (A)

| Rank | Sequence | Position | Score | |
|------|----------|----------|--------|--|
| 1 | K S P F S R L T | 68 | 63.646 | SEQ ID NO 14 |
| 2 | R S P F N R _ T | 68 | 12.659 | SEQ ID NO 15 |
| 3 | Y S S P F N R K | 67 | 8.382 | SEQ ID NO 16 |
| 4 | H R S P F N R K | 67 | 1.947 | SEQ ID NO 17 |
| 5 | I S E Y K L R L | 103 | 0.789 | SEQ ID NO 18 |
| 6 | K S P F S R L T | 68 | 0.252 | SEQ ID NO 19 |
| 7 | S P F S R L T C | 69 | 0.252 | SEQ ID NO 20 |
| 8 | Y R S P F N R K | 67 | 0.163 | SEQ ID NO 21 |
| 9 | K S P F S R L T | 68 | 0.126 | SEQ ID NO 22 |
| 10 | S P F S R L T S | 69 | 0.126 | SEQ ID NO 23 |

(B)

MEVGWYRSPFSRVVHLYRNGK   SEQ ID NO 1

(C)

SEQUENCE LISTING

<160> NUMBER OF SEQ ID NOS: 23

<210> SEQ ID NO 1
<211> LENGTH: 21
<212> TYPE: PRT
<213> ORGANISM: Mus musculus

<400> SEQUENCE: 1

Met Glu Val Gly Trp Tyr Arg Ser Pro Phe Ser Arg Val Val His Leu
1               5                   10                  15

Tyr Arg Asn Gly Lys
            20

<210> SEQ ID NO 2
<211> LENGTH: 66
<212> TYPE: DNA
<213> ORGANISM: Artificial Sequence
<220> FEATURE:
<223> OTHER INFORMATION: random library DNA
<220> FEATURE:
<221> NAME/KEY: misc_feature
<222> LOCATION: (19)..(42)
<223> OTHER INFORMATION: n is a, g, c or t ; m is a or c

<400> SEQUENCE: 2
gctgccgctg ccgctgccmn nmnnmnnmnn mnnmnnmnnm nncatatgta tatctccttc      60
ttaaag                                                                66

<210> SEQ ID NO 3
<211> LENGTH: 50

```
<212> TYPE: DNA
<213> ORGANISM: Artificial Sequence
<220> FEATURE:
<223> OTHER INFORMATION: primer

<400> SEQUENCE: 3
cctaatacga ctcactatag ggttaacttt aagaaggaga tatacatatg          50

<210> SEQ ID NO 4
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(2)
<223> OTHER INFORMATION: gm

<400> SEQUENCE: 4
ggtcggcgga tcaaagtagc tgccgctgcc gctgccgca                      39

<210> SEQ ID NO 5
<211> LENGTH: 113
<212> TYPE: DNA
<213> ORGANISM: Artificial Sequence
<220> FEATURE:
<223> OTHER INFORMATION: random DNA library
<220> FEATURE:
<221> NAME/KEY: misc_feature
<222> LOCATION: (51)..(74)
<223> OTHER INFORMATION: n is a, g, c or t ; k is g or t

<400> SEQUENCE: 5
cctaatacga ctcactatag ggttaacttt aagaaggaga tatacatatg nnknnknnkn   60
nknnknnknn knnktgcggc agcggcagcg gcagctactt tgatccgccg acc         113

<210> SEQ ID NO 6
<211> LENGTH: 16
<212> TYPE: DNA
<213> ORGANISM: Artificial Sequence
<220> FEATURE:
<223> OTHER INFORMATION: Pu-DNA

<400> SEQUENCE: 6
ctcccgcccc ccgtcc                                               16

<210> SEQ ID NO 7
<211> LENGTH: 23
<212> TYPE: DNA
<213> ORGANISM: Artificial Sequence
<220> FEATURE:
<223> OTHER INFORMATION: splint DNA

<400> SEQUENCE: 7
gggcgggagg gtcggcggat caa                                       23

<210> SEQ ID NO 8
<211> LENGTH: 39
<212> TYPE: DNA
<213> ORGANISM: Artificial Sequence
<220> FEATURE:
<223> OTHER INFORMATION: primer

<400> SEQUENCE: 8
ggtcggcgga tcaaagtagc tgccgctgcc gctgccgca                      39
```

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ccgaaggaga tatacatatg                                                  20

<210> SEQ ID NO 10
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(3)
<223> OTHER INFORMATION: n is a, g, c or t

<400> SEQUENCE: 10
annctgccgc tgccgctgc                                                   19

<210> SEQ ID NO 11
<211> LENGTH: 107
<212> TYPE: DNA
<213> ORGANISM: Artificial Sequence
<220> FEATURE:
<223> OTHER INFORMATION: Flag DNA

<400> SEQUENCE: 11
ggcgtaatac gactcactat agggttaact ttaacaagga gaaaacatg aagtactccc       60 caaccgactg cggcagcggc agcggcagct actttgatcc gccgacc                   107

<210> SEQ ID NO 12
<211> LENGTH: 140
<212> TYPE: DNA
<213> ORGANISM: Artificial Sequence
<220> FEATURE:
<223> OTHER INFORMATION: Template DNA 1

<400> SEQUENCE: 12
cctaatacga ctcactatag ggttaacttt aagaaggaga tatacatatg aagtactccc      60
caaccgactg caagaaggac tacaaggacg acgacgacaa gtgcggcagc ggcagcggca     120
gctaggacgg ggggcggaaa                                                 140

<210> SEQ ID NO 13
<211> LENGTH: 140
<212> TYPE: DNA
<213> ORGANISM: Artificial Sequence
<220> FEATURE:
<223> OTHER INFORMATION: Template DNA 2 & 3

<400> SEQUENCE: 13
cctaatacga ctcactatag ggttaacttt aagaaggaga tatacatatg aagtactccc      60
caaccgactg caagaaggac tacaaggacg acgacgacaa gtgcggcagc ggcagcggca     120
gctactttga tccgccgacc                                                 140

<210> SEQ ID NO 14
<211> LENGTH: 8
<212> TYPE: PRT
<213> ORGANISM: Artificial Sequence

```
<220> FEATURE:
<223> OTHER INFORMATION: peptide derived from random DNA

<400> SEQUENCE: 14

Lys Ser Pro Phe Ser Arg Leu Thr
1               5

<210> SEQ ID NO 15
<211> LENGTH: 6
<212> TYPE: PRT
<213> ORGANISM: Artificial Sequence
<220> FEATURE:
<223> OTHER INFORMATION: peptide derived from random DNA

<400> SEQUENCE: 15

Arg Ser Pro Phe Asn Arg
1               5

<210> SEQ ID NO 16
<211> LENGTH: 8
<212> TYPE: PRT
<213> ORGANISM: Artificial Sequence
<220> FEATURE:
<223> OTHER INFORMATION: peptide derived from random DNA

<400> SEQUENCE: 16

Tyr Ser Ser Pro Phe Asn Arg Lys
1               5

<210> SEQ ID NO 17
<211> LENGTH: 8
<212> TYPE: PRT
<213> ORGANISM: Artificial Sequence
<220> FEATURE:
<223> OTHER INFORMATION: peptide derived from random DNA

<400> SEQUENCE: 17

His Arg Ser Pro Phe Asn Arg Lys
1               5

<210> SEQ ID NO 18
<211> LENGTH: 8
<212> TYPE: PRT
<213> ORGANISM: Artificial Sequence
<220> FEATURE:
<223> OTHER INFORMATION: peptide derived from random DNA

<400> SEQUENCE: 18

Ile Ser Glu Tyr Lys Leu Arg Leu
1               5

<210> SEQ ID NO 19
<211> LENGTH: 8
<212> TYPE: PRT
<213> ORGANISM: Artificial Sequence
<220> FEATURE:
<223> OTHER INFORMATION: peptide derived from random DNA

<400> SEQUENCE: 19

Lys Ser Pro Phe Ser Arg Leu Thr
1               5

<210> SEQ ID NO 20
<211> LENGTH: 8
<212> TYPE: PRT
<213> ORGANISM: Artificial Sequence
<220> FEATURE:
```

```
<223> OTHER INFORMATION: peptide derived from random DNA

<400> SEQUENCE: 20

Ser Pro Phe Ser Arg Leu Thr Cys
1               5

<210> SEQ ID NO 21
<211> LENGTH: 8
<212> TYPE: PRT
<213> ORGANISM: Artificial Sequence
<220> FEATURE:
<223> OTHER INFORMATION: peptide derived from random DNA

<400> SEQUENCE: 21

Tyr Arg Ser Pro Phe Asn Arg Lys
1               5

<210> SEQ ID NO 22
<211> LENGTH: 8
<212> TYPE: PRT
<213> ORGANISM: Artificial Sequence
<220> FEATURE:
<223> OTHER INFORMATION: peptide derived from random DNA

<400> SEQUENCE: 22

Lys Ser Pro Phe Ser Arg Leu Thr
1               5

<210> SEQ ID NO 23
<211> LENGTH: 8
<212> TYPE: PRT
<213> ORGANISM: Artificial Sequence
<220> FEATURE:
<223> OTHER INFORMATION: peptide derived from random DNA

<400> SEQUENCE: 23

Ser Pro Phe Ser Arg Leu Thr Ser
1               5
```

METHOD FOR PRODUCING COMPLEX OF RNA MOLECULE AND PEPTIDE, AND UTILIZATION THEREOF

CROSS REFERENCE TO RELATED APPLICATIONS

This application is a U.S. National Stage application of PCT/JP2018/010223 filed on Mar. 15, 2018, which claims priority to Japanese patent application 2017-053621 filed on Mar. 17, 2017, the contents of both of which are incorporated herein by reference.

TECHNICAL FIELD

The present invention relates to a method for producing a complex of an RNA molecule and a peptide encoded by the RNA molecule, utilization thereof, and the like.

BACKGROUND ART

In recent years, development of molecularly-targeted drugs typified by antibody drugs have been actively conducted, and a market for the molecularly-targeted drugs has been expanding. For further development and expansion, however, there is a demand for a technique that enables efficiently selecting a "high quality antibody" that has higher specificity and higher affinity for an antigen. Further, there are many intractable diseases and chronic diseases whose causes are yet to be identified. Research into the causes has been conducted but unsuccessful. Thus, "depletion of drug discovery targets" has been recognized as a problem.

Generally, protein analysis is more difficult than gene analysis. This is due to, for example, a fact that whereas various gene amplification methods (e.g., PCR) have been developed to enable easy preparation of samples in large quantities, there is no means for directly amplifying proteins.

In view of this, there has been developed, as an example method for facilitating protein analysis, a method that uses a complex in which a protein and a gene encoding the protein are directly bound.

For example, Patent Literature 1 and Non-patent Literatures 1 and 2 disclose techniques in each of which a functional peptide is selected with use of a complex in which a gene (mRNA) and a peptide as a translation product thereof are linked by a covalent bond via puromycin. More specifically, puromycin is linked via a predetermined linker to a gene (mRNA) on a 3' end side of the gene, and the gene is translated so that the gene (mRNA) and a peptide as a translation product thereof are linked via the puromycin. The techniques, which are also referred to as "mRNA display method", "in vitro virus", etc., enable using an enormous library containing approximately $10^{13}$ to $10^{14}$ complexes. Further, methods derived from the above method have also been developed, such as (i) cDNA display in which mRNA is converted to cDNA to be used and (ii) RAPID display in which unnatural amino acids can be used.

As a method for linking a gene (mRNA) to puromycin or an alternative thereof (generally referred to as a "peptide receptor molecule" or a "peptide acceptor") in the mRNA display method, several methods have been developed. At the time when the mRNA display method was developed, a method using a DNA called "splint DNA" as an anchorage was a mainstream method. In this method, more specifically, the above-described linker containing the peptide receptor molecule and the 3' end side of the gene (mRNA) are caused to hybridize with the same splint DNA to achieve enzymatic ligation of the linker and the 3' end side of the gene (mRNA) (Non-patent Literature 3 etc.).

However, it has currently become mainstream to employ, as a method for linking a gene (mRNA) and a peptide receptor molecule, a method employing a linker which has, at one end thereof, a side chain base pairing with a base sequence positioned on a 3' end side of the mRNA and has, at the other end thereof, a peptide receptor molecule (see Patent Literature 2 etc.). When this linker is used, the one end of the linker hybridizes with the base sequence on the 3' end side of the mRNA and then the one end of the linker and the 3' end of the mRNA are enzymatically linked to form a hairpin structure.

CITATION LIST

Patent Literatures

[Patent Literature 1]
International Publication No. WO98/31700 (Publication Date: Jul. 23, 1998)
[Patent Literature 2]
International Publication No. WO2011/049157 (Publication Date: Apr. 28, 2011)

Non-Patent Literatures

[Non-Patent Literature 1]
RNA-peptide fusions for the in vitro selection of peptides and proteins. Proc. Natl. Acad. Sci. USA, 94: 12297-12302, 1997.
[Non-Patent Literature 2]
In vitro virus: Bonding of mRNA bearing puromycin at the 3'-terminal end to the C-terminal end of its encoded protein on the ribosome in vitro. FEBS Letters 414: 405-408, 1997.
[Non-Patent Literature 3]
Optimized Synthesis of RNA-Protein Fusions for in Vitro Protein Selection. METHODS IN ENZYMOLOGY, VOL. 318, P268-293, 2000.

SUMMARY OF INVENTION

Technical Problem

The method as disclosed in Non-patent Literature 3 etc. of using a splint DNA has a problem that a failure to strictly control both of the base sequence on the 3' end side of the gene (mRNA) and the base sequence of the linker containing puromycin results in a significant decrease in efficiency of ligation of these base sequences.

The method as disclosed in Patent Literature 2 etc. of linking (forming a hairpin structure) a gene (mRNA) and a peptide receptor molecule is superior to the method using a splint DNA in that 1) no splint DNA is necessary and 2) there is some tolerance with respect to exactness of hybridization of the base sequence of the one end of the linker and the base sequence on the 3' end side of the mRNA (enzymatic linking is still possible even if one or several bases are misaligned).

However, the mRNA display method is a method including various steps in addition to the step of linking a gene (mRNA) and a peptide receptor molecule. As such, from the viewpoint of efficiently obtaining a complex in which a gene (mRNA) and a peptide as a translation product thereof are linked, the mRNA display method is likely to have much room for improvement.

It is an object of an aspect of the present invention to provide: a method for efficiently obtaining a complex in which a gene (mRNA) and a peptide as a translation product thereof are linked via a peptide receptor molecule; and utilization of thereof.

Solution to Problem

The inventors of the present invention conducted diligent study on the above problems. As a result, the inventors have discovered an unexpected possibility that the method of linking a gene (mRNA) and a peptide receptor molecule with use of a splint DNA is superior from the viewpoint of efficiently obtaining a complex of a gene (mRNA) and a peptide as a translation product thereof. From this knowledge, the inventors redirected their attention to the method of using a splint DNA and consequently arrived at the present invention.

In order to attain the object, an aspect of the present invention is as follows.

(1) A method for producing a complex of an RNA molecule encoding a peptide and the peptide encoded by the RNA molecule, the method including the steps of: (i) producing the RNA molecule from a DNA molecule via transcription, the DNA molecule (a) containing a promoter region and a region that is located downstream of the promoter region and encodes the peptide and (b) containing at least one 2'-modified nucleoside derivative on a 5' end side of an antisense strand that is located most downstream; (ii) binding, to a 3' end of the RNA molecule obtained in the step (i), a peptide receptor molecule with use of a splint polynucleotide as an anchorage; and (iii) performing translation of the RNA molecule, to which the peptide receptor molecule has been bound through the step (ii), to produce the complex in which the receptor molecule and the peptide encoded by the RNA molecule are linked via the peptide receptor molecule.

(2) A DNA library for use in an mRNA display method, containing: a plurality of different candidate DNA molecules, each of the plurality of different candidate DNA molecules (i) containing a promoter region and a region that is located downstream of the promoter region and encodes a candidate peptide and (ii) containing at least one 2'-modified nucleoside derivative on a 5' end side of an antisense strand that is located most downstream.

Advantageous Effects of Invention

An aspect of the present invention enables providing: a method for efficiently obtaining a complex in which a gene (mRNA) and a peptide as a translation product thereof are linked via a peptide receptor molecule; and utilization thereof.

DESCRIPTION OF EMBODIMENTS

A method in accordance with the present invention for producing a complex of an RNA molecule encoding a peptide and the peptide encoded by the RNA molecule is a method including the steps of: (i) producing the RNA molecule from a DNA molecule via transcription, the DNA molecule (a) containing a promoter region and a region that is located downstream of the promoter region and encodes the peptide and (b) containing at least one 2'-modified nucleoside derivative on a 5' end side of an antisense strand that is located most downstream; (ii) binding, to a 3' end of the RNA molecule obtained in the step (i), a peptide receptor molecule with use of a splint polynucleotide as an anchorage; and (iii) performing translation of the RNA molecule, to which the peptide receptor molecule has been bound through the step (ii), to produce the complex in which the receptor molecule and the peptide encoded by the RNA molecule are linked via the peptide receptor molecule.

The description below deals with an embodiment of the present invention in detail.

Definition

In the present specification, the term "library" refers to a set of a plurality of (two or more) different molecules (e.g., a plurality of different DNA molecules, a plurality of different RNA molecules, or a plurality of different RNA-peptide complexes). For example, a "library" refers to a set of a plurality of different molecules belonging to the same category (e.g., a category of DNA molecule, a category of RNA molecule, or a category of RNA-peptide complex). In relation to a name of a molecule category, a "library" may be referred to as a "DNA library" (a library of DNA molecules), an "RNA library" (a library of RNA molecules), an RNA-peptide complex library (a library of RNA-peptide complex molecules), or the like. Because a method in accordance with the present embodiment facilitates selections which begin, if desired, with large numbers of candidate molecules, a "library" in accordance with the present embodiment may contain preferably $10^9$ or more, more preferably $10^{10}$ or more, $10^{11}$ or more, or $10^{12}$ or more, even more preferably $10^{13}$ or more different molecules.

The term "selection" refers to substantially partitioning a molecule from other molecules in a population. For example, "selection" refers to substantially partitioning a molecule from other molecules in a set of a plurality of different molecules that belong to the same category. As used herein, "selection" can provide at least a 2-fold, preferably, a 30-fold or more, more preferably, a 100-fold or more, and, even more preferably, a 1000-fold or more enrichment of a desired molecule relative to undesired molecules in a library following the selection. As indicated herein, a selection step may be repeated any number of times, and different types of selection steps may be combined in a given approach.

Conventional Method

Figure 1:
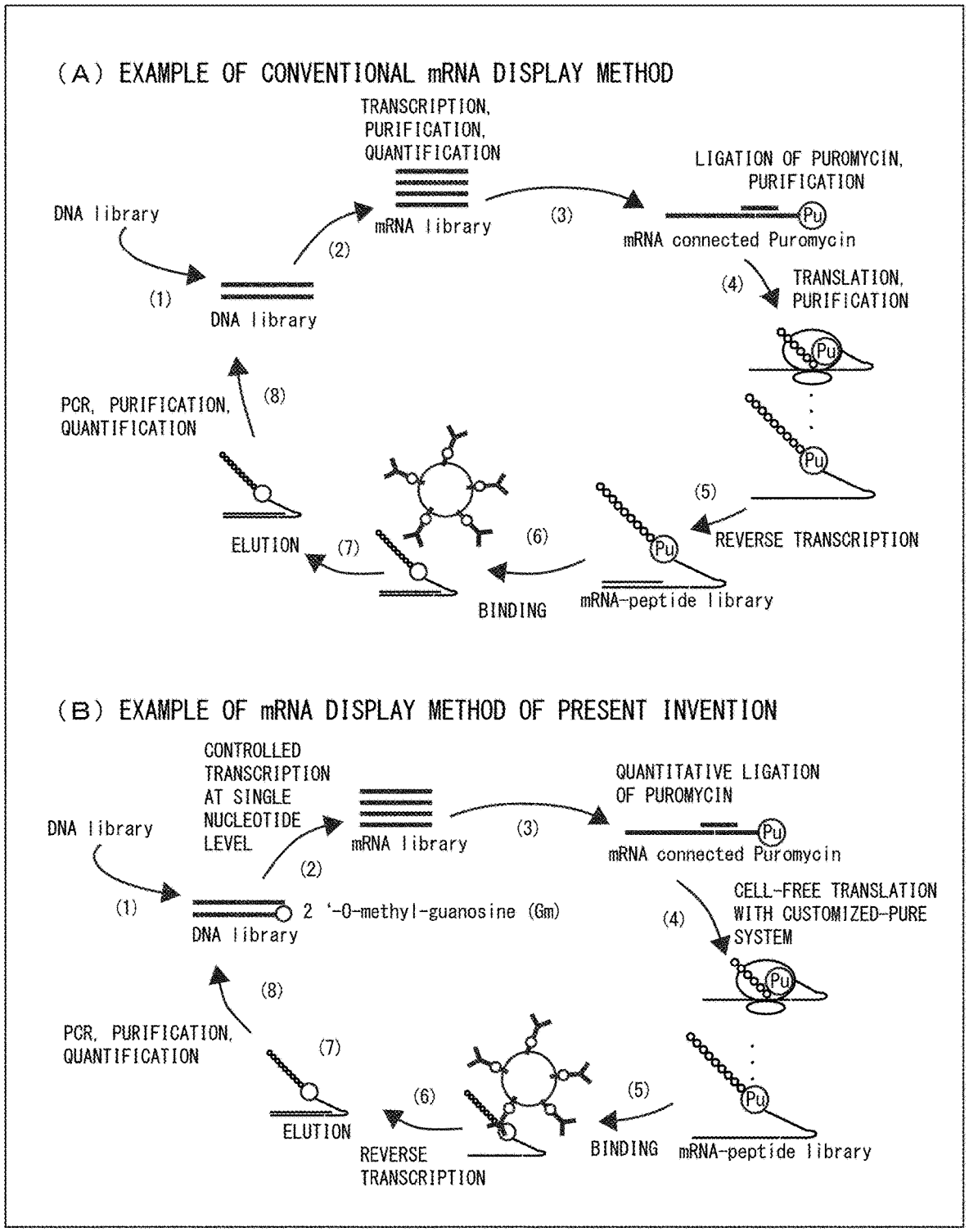
FIG. 1 is a view illustrating differences between an example conventional method and an example method of the present invention.

Before describing a method in accordance with the present embodiment, the following description will first briefly discuss, with reference to (A) of FIG. 1, an example conventional mRNA display method which uses a splint polynucleotide (DNA).

In the example mRNA display method, the following steps are carried out.

(1) First, a library containing candidate DNA molecules encoding respective candidate peptides is prepared. Each of the candidate DNA molecules is ordinarily double-stranded and has a structure in which a region encoding a corresponding peptide is located downstream of a promoter region recognized by RNA polymerase which is used in a transcription reaction in a step (2). Upstream of the region encoding the peptide, there is a translation initiation sequence (e.g., a start codon) suitable for a cell-free translation system which is used.

(2) Subsequently, RNA polymerase is caused to act on each of the candidate DNA molecules to cause a transcription reaction. Thus produced is a library of corresponding candidate RNA molecules. Then, the candidate RNA molecules produced are each separated from other components of the transcription reaction.

(3) Subsequently, a linker, to a 3' end of which a peptide receptor molecule (e.g., puromycin) is bonded, is ligated to a 3' end of each candidate RNA molecule. The linker contains a nucleotide, to a 3' end of which the peptide receptor molecule is bonded. Polyethylene glycol (PEG) may be inserted in between the nucleotide and the peptide receptor molecule. For binding the candidate RNA molecule and the linker together, an oligonucleotide (e.g., "splint DNA") referred to as a "splint polynucleotide" may be used. In such a case, a splint polynucleotide containing a sequence capable of hybridizing with the 3' end side of the candidate RNA molecule and a sequence capable of hybridizing with a 5' end side of the nucleotide of the linker is used as an anchorage. That is, the splint polynucleotide contains (i) a sequence complementary to a sequence on a 5' end side of the linker and (ii) a sequence which is adjacent to this sequence of the splint polynucleotide and is complementary to a sequence on the 3' end side of the candidate RNA molecule. The candidate RNA molecule and the linker, which are linked via the splint polynucleotide, are ligated (bound) by a reaction in which, for example, T4 DNA ligase is used. Note that due to a characteristic of the RNA polymerase used in the step (2), one or several bases are added to the 3' end of the candidate RNA molecule at a given frequency (e.g., approximately 50%). Accordingly, the library produced contains candidate RNA molecules each having one or several bases added to a 3' end thereof. This non-uniformity of 3' end sequence can cause a decrease in ligation efficiency. Subsequently, purification is carried out to remove an unligated candidate RNA molecule. Failure to remove the unligated candidate RNA molecule at this stage causes a peptide that does not form a complex with RNA to be produced in a step (4), so that an efficiency of obtaining a desired candidate RNA-peptide complex is decreased when the peptide is brought into contact with a binding partner in a step (6).

(4) Subsequently, the candidate RNA molecule is translated in a cell-free translation system to produce a candidate RNA-peptide complex in which the candidate RNA molecule and a candidate peptide corresponding to the candidate RNA molecule are linked via the linker. Then, purification is carried out in order to remove impurities (high concentration Mg, K, and the like) in the cell-free translation system so that a reverse transcription reaction can be carried out in a step (5).

(5) Subsequently, with an aim to, for example, prevent degradation caused by RNase, a reverse transcription reaction is carried out so that the candidate RNA molecule of the candidate RNA-peptide complex forms a double-stranded region with a DNA (cDNA) molecule. Thus produced is a library of candidate RNA-peptide complexes.

(6) Subsequently, the candidate RNA-peptide complexes in the library are each brought into contact with a binding partner (e.g., an antibody immobilized on a solid support, or the like) to carry out a binding reaction. Candidate RNA-peptide complexes unbound to the binding partner are removed by, for example, being washed using a buffer or the like.

(7) Subsequently, each candidate RNA-peptide complex is dissociated from the binding partner and recovered. Thus, a desired RNA-peptide complex is selected from the library of candidate RNA-peptide complexes.

(8) Subsequently, amplification of cDNA is conducted by PCR. Starting back from the step (2), the procedure is similarly repeated using an amplification product obtained by the amplification. This enables enrichment of a desired candidate RNA-peptide complex.

Method of Present Embodiment

The following description will discuss in detail, with reference to (B) of FIG. 1, an mRNA display method in which a method in accordance with the present embodiment is used.

[Step 1]

In Step 1, a library of candidate DNA molecules is prepared. The library contains a plurality of different candidate DNA molecules each containing a promoter region and a region which (i) is located downstream of the promoter region and (ii) encodes a candidate peptide. Further, the plurality of different candidate DNA molecules each contain at least one 2'-modified nucleoside derivative on a 5' end side of an antisense strand that is located most downstream.

In the present specification, the term "polypeptide" refers to a compound formed from two or more amino acids bound together by a peptide bond. The number of amino acids is not limited, and may be, for example, 2 to 1000, preferably 4 to 200, more preferably 6 to 100, even more preferably 7 to 10. The peptide may be, for example, a fragment or a full length of a protein. In one example, the peptide may be an antibody (scFv or the like) or a fragment thereof.

Each candidate DNA molecule may be a molecule whose sequence is known, or may be a molecule whose sequence is unknown. As genome information, the sequence may be a sequence that is based on a naturally occurring sequence (e.g., a cDNA into which a naturally occurring mRNA is reverse transcribed), or may be an artificially designed sequence. For example, the candidate DNA molecule may have a sequence randomly synthesized by organic synthesis, or may be a sequence which, as a result of insertion of random mutation into the sequence using PCR, encodes a protein whose sequence is unknown.

The candidate DNA molecule contains the region encoding the candidate peptide. The candidate DNA molecule contains, as necessary, a region (transcriptional regulatory region) for carrying out transcription with use of an antisense strand as a template. Examples of the transcriptional regulatory region contain the promoter region. The transcriptional regulatory region may be selected from those examples as appropriate, in accordance with a type of RNA polymerase used in a transcription reaction in Step 2. In one example, the promoter region may be a region (T7 promoter, SP6 promoter, or T3 promoter) recognized by T7 RNA polymerase, SP6 RNA polymerase, or T3 RNA polymerase.

The candidate DNA molecule, which contains the promoter region and the region located downstream of the promoter region and encoding the candidate peptide, may be single-stranded or double-stranded, or both (part of the candidate DNA molecule is double-stranded and a rest of the candidate DNA molecule is single-stranded), provided that a candidate RNA molecule encoding the peptide is produced by a transcription reaction.

Specifically, the promoter region in the candidate DNA molecule may be single-stranded or double-stranded, or both, provided that a candidate RNA molecule encoding the candidate peptide is transcribed from the region located downstream of the promoter region and encoding the candidate peptide. For example, the promoter region may have such a structure that part of the promoter region is constituted by a single strand (a sense strand or an antisense strand) and the rest of the promoter region is double-stranded. Such a promoter region partially constituted by a single strand (a sense strand or an antisense strand) is also encompassed in the scope of the "promoter region" in the present specification. A promoter region that exhibits promoter activity enables transcription into a candidate RNA molecule encoding the candidate peptide. Promoter activity can be measured by a well-known method in the field. Transcription into a candidate RNA molecule encoding the candidate peptide can be recognized by detection of an RNA molecule, detection of a peptide produced by translation, or the like carried out by a well-known method in the field.

Further, the region encoding the candidate peptide in the candidate DNA molecule may be single-stranded or double-stranded, or both, provided that a candidate RNA molecule encoding the candidate peptide is transcribed by a function of the promoter region located upstream of the region encoding the candidate peptide. For example, an entire coding region may be single-stranded (a sense strand or an antisense strand). Since the candidate RNA molecule is transcribed based on a sequence of an antisense strand as a template, the region encoding the candidate peptide preferably contains at least an antisense strand. Such a coding region partially or entirely constituted by a single strand (a sense strand or an antisense strand) is also encompassed in the scope of the "region encoding a peptide" in the present specification. Containing at least an antisense strand in the region encoding the candidate peptide is preferable also from the viewpoint of enabling at least one 2'-modified nucleoside derivative to be contained on a 5' end side of the downstream-most antisense strand of the candidate DNA molecule.

The candidate DNA molecule contains, as necessary, a sequence for translation of the candidate RNA molecule. The sequence for translation of the candidate RNA molecule may be selected as appropriate in accordance with a type of a ribosome used in Step 4. In a case where a ribosome derived from *E. coli* is used as a cell-free translation system, the efficiency of translation reaction is increased by including, in a position upstream of a start codon, a Shine-Dalgarno (SD) sequence which is a ribosomal binding sequence. In a case where a cell-free translation system derived from a eukaryote is used, the candidate DNA molecule may contain a Kozak sequence which promotes translation initiation. In the transcription reaction at Step 2, a 7-methylguanosine cap structure may be added to the 5' end of the candidate DNA molecule. Other sequences for transcription and for translation can be selected as appropriate by a person skilled in the art.

In Step 2 (described later), transcription of the candidate DNA molecules is carried out. A method of the transcription is not particularly limited. In a case where transcription of all candidate DNA molecules in the library of candidate DNA molecules is carried out in a single reaction system, it is preferable that a sequence of a transcriptional regulatory region be identical among all candidate DNA molecules in the library of candidate DNA molecules. In Step 4 (described later), translation of candidate RNA molecules is carried out. A method of the translation is not particularly limited. In a case where translation of all candidate RNA molecules in a library of candidate RNA molecules is carried out in a single reaction system, it is preferable that a sequence for translation of a candidate RNA molecule be identical among all candidate DNA molecules in the library of candidate DNA molecules. In Step 3 (described later), ligation of a 3' end of a candidate RNA molecule and a 5' end of an oligonucleotide of a linker is carried out using a splint polynucleotide as an anchorage. In a case where ligation of all candidate RNA molecules in a library of candidate RNA molecules is carried out in a single reaction system, it is preferable that, among all candidate DNA molecules in the library of candidate DNA molecules, a sequence corresponding to a sequence which is (i) positioned on a 3' end side of a candidate RNA molecule and (ii) used for hybridization with a splint polynucleotide be identical. As such, in a preferable example, among all candidate DNA molecules in the library of candidate DNA molecules, one, two, or all three of the following (a) to (c) are identical: (a) a sequence of a transcriptional regulatory region, (b) a sequence for translation of a candidate RNA molecule, and (c) a sequence corresponding to a sequence which is (i) located on a 3' end side of a candidate RNA molecule and (ii) used for hybridization with a splint polynucleotide.

In a more preferable example, among all candidate DNA molecules in the library of candidate DNA molecules, a sequence of a region other than a sequence in an open reading frame (ORF) region is identical. It is a well-known technique that, in order to allow (i) preparation of a library of cDNAs into which naturally occurring mRNAs are reverse transcribed and (ii) preparation of an artificially designed library of DNAs to use (a) a common primer set in DNA amplification, (b) a common transcription system in DNA-to-RNA transcription, and/or (c) a common translation system in RNA-to-peptide translation, all candidate DNAs contained in a library share a common sequence at a site closer to a 5' end than an ORF region and share another common sequence at a site closer to a 3' end than the ORF region.

One of the characteristics of methods in accordance with the present embodiment is that a candidate DNA molecule contains at least one 2'-modified nucleoside derivative on a 5' end side of an antisense strand. It is preferable that the candidate DNA molecule contain consecutive two 2'-modified nucleoside derivatives. It is preferable that one of the at least one 2'-modified nucleoside derivative be located at the second position from the 5' end of the antisense strand of the candidate DNA molecule. In a case where the candidate DNA molecule contains two or more 2'-modified nucleoside derivatives, one of the two or more 2'-modified nucleoside derivatives is preferably located at the 5' end. Alternatively, one of the at least one 2'-modified nucleoside derivative is located at the 5' end of the antisense strand of the candidate DNA molecule.

The 5' end of the antisense strand is located on an opposite side to the promoter region across the region encoding the peptide. Accordingly, the antisense strand has the following structure: (promoter region)-(region encoding the candidate peptide)-(at least one 2'-modified nucleoside derivative) arranged in this order from the 3' end side (note that another sequence may be included in between). Thus, the at least one 2'-modified nucleoside derivative is located downstream in a transcription direction.

Modification at 2' is not particularly limited, but may be, for example, an alkoxy group having 1 to 10 carbon atoms, a halogen group, an ester group having 1 to 10 carbon atoms, or the like.

The at least one 2'-modified nucleoside derivative is preferably 2'-O-methyl nucleoside (e.g., 2'-O-methyladenosine, 2'-O-methylguanosine, 2'-O-methyl thymidine, 2'-O-methylcytidine, 2'-O-methyluridine, and 2'-O-methylinosine, or the like), more preferably 2'-O-methylguanosine. 2'-O-methylguanosine (Gm) is represented by the following structural formula.

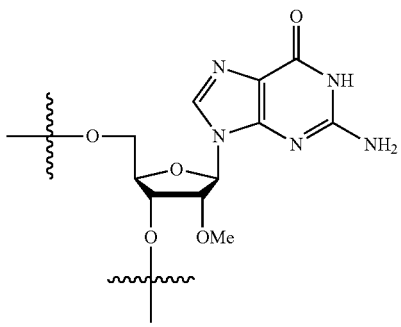

A method for producing such a candidate DNA is not particularly limited. Examples of the method include a method in which a Reverse primer, in which at least one nucleoside on a 5' end side has been substituted by a 2'-modified nucleoside derivative, and an ordinary Forward primer are used to conduct a PCR reaction with respect to a library of candidate DNA molecules in each of which no nucleoside on a 5' end side has been substituted by a 2'-modified nucleoside derivative. It is preferable that a nucleoside at the 5' end and a nucleoside at the second position from the 5' end of the Reverse primer are each substituted by a 2'-modified nucleoside derivative.

[Step 2]

In Step 2, the candidate DNA molecules are transcribed as templates to produce a library of corresponding RNA molecules (an aspect of the "step (i)").

Transcription can be conducted by a well-known method. Typically, the transcription is carried out in situ or in vitro, preferably in vitro. In a case where the transcription is carried out in vitro, a type of RNA polymerase is not particularly limited. Preferable examples of the RNA polymerase include an RNA polymerase derived from bacteriophage, such as T7 RNA polymerase, SP6 RNA polymerase, T3 RNA polymerase, and the like. In particular, T7 RNA polymerase is more preferable.

Note that in the present embodiment, at least one 2'-modified nucleoside derivative is present on the 5' end side of the antisense strand which serves as a template for RNA. This reduces occurrence of a phenomenon in which one or several bases not corresponding to the DNA template are added to the 3' end of the RNA. In the present embodiment, therefore, occurrence of addition of a base can be effectively reduced even in a case where the above-described RNA polymerase which is prone to cause addition of a base is used. In a preferable example, 60% or more, 70% or more, 80% or more, or 90% or more of candidate RNA molecules in the library of candidate RNA molecules do not have a base added thereto.

In a preferable example, all candidate RNAs in the library of candidate RNA molecules are identical in (a) a sequence of a transcriptional regulatory region and/or (b) a sequence that is positioned on a 3' end side and used for hybridization with a splint polynucleotide.

In the conventional method, one or several bases are added to a 3' end of a candidate RNA molecule due to a characteristic of the RNA polymerase used. This causes a decrease in binding efficiency of the linker in the step (3). In order to solve this problem, a technique was developed in which (i) a linker which is complementary to a 3' end region of the candidate RNA and to the 3' end of which puromycin is bound is caused to hybridize with the 3' end region of the candidate RNA and (ii) then the 3' end region of the candidate RNA and the linker are linked by ligation with use of T4 RNA ligase to form a hairpin structure. Also devised was a method of conducting purification of the library by high-resolution electrophoresis to remove a candidate RNA molecule to which one or several bases have been added. In contrast, the method of the present embodiment enables a peptide receptor molecule to be bound more easily and efficiently in Step 3 (described later) without conducting purification.

[Step 3]

In Step 3, a peptide receptor molecule is bound to the 3' end of the candidate RNA molecule with use of a splint polynucleotide as an anchorage (an aspect of the "step (ii)").

The "peptide receptor molecule" is not particularly limited, provided that the peptide receptor molecule can be linked to the peptide which has been translated. Examples of the peptide receptor molecule encompass well-known peptide receptor molecules such as puromycin, a puromycin derivative, and an oligo RNA-amino acid complex (e.g., a peptide acceptor region described in WO2011/049157). Puromycin (Pu) is represented by the following structural formula.

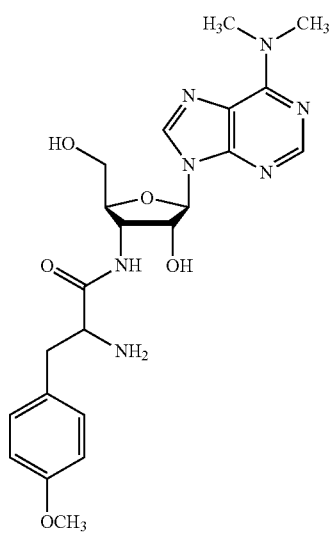

The 3' end of the candidate RNA molecule and the puromycin are typically bound together via a linker containing an oligonucleotide. A length of the oligonucleotide is not particularly limited. For example, the oligonucleotide consists of approximately 10 to 30 nucleotides, preferably 15 to 20 nucleotides. Examples of a nucleotide contained in the oligonucleotide include DNA, RNA, PNA, LNA, and the like. The linker may have inserted therein another substance (e.g., polyethylene glycol (PEG)) in addition to the oligonucleotide. A length of the PEG is not particularly limited. In one example, the PEG is preferably formed by linking 3 to 10 units each of which has a main chain having 6 to 18 atoms. In one example, the linker may have the following structure: 5'-(oligonucleotide)-(PEG)-(peptide receptor molecule)-3'. Such a linker may be produced by a well-known method.

The splint polynucleotide contains a sequence capable of hybridizing with the 3' end side of the candidate RNA molecule and a sequence capable of hybridizing with the 5' end side of the oligonucleotide of the linker. Accordingly, in a case where the candidate RNA molecule, the linker containing the peptide receptor molecule and the oligonucleotide, and the splint polynucleotide coexist, the 3' end side of the candidate RNA molecule hybridizes with the 5' end side of the splint polynucleotide and the 5' end side of the oligonucleotide hybridizes with the 3' end side of the splint polynucleotide. Then, the 3' end of the candidate RNA molecule and the 5' end of the oligonucleotide are ligated with each other with use of, for example, DNA ligase (T4 DNA ligase or the like), RNA ligase (T4 RNA ligase or the like), or the like.

Examples of a nucleotide contained in the splint polynucleotide include DNA, RNA, PNA, LNA, and the like. In one example, the nucleotide is preferably DNA from the viewpoint that DNA can be used also as a primer in reverse transcription.

The splint polynucleotide, for example, contains approximately 14 to 40 consecutive nucleotides. In one example, consecutive nucleotides (for example, approximately 7 to 20, preferably 9 to 15 consecutive nucleotides) on the 5' end side of the splint polynucleotide hybridize with the sequence on the 3' end side of the candidate RNA molecule, and consecutive nucleotides (for example, approximately 7 to 20, preferably 9 to 15 consecutive nucleotides) on the 3' end side of the splint polynucleotide hybridize with the sequence on the 5' end side of the oligonucleotide of the linker. In a particularly preferable example, the splint polynucleotide is designed so that, in a state where the candidate RNA molecule and the oligonucleotide of the linker hybridize with the splint polynucleotide, there is no gap (missing nucleotide) between the splint polynucleotide and the 3' end of the candidate RNA molecule and between the splint polynucleotide and the 5'-terminal side of the oligonucleotide of the linker.

In the present embodiment, occurrence of addition of a base in the candidate RNA is reduced as described above. This enables an improvement in ligation efficiency. As such, it is not necessary to carry out purification for removal of candidate RNA molecules unbound to the peptide receptor molecule. In contrast, the conventional method has poor ligation efficiency, thus making it necessary to remove an unligated candidate RNA molecule. Failure to remove the unligated candidate RNA molecule causes a peptide that does not form a complex with RNA to be produced during translation, so that an efficiency of obtaining an intended candidate RNA-peptide complex is decreased when the peptide is later brought into contact with a binding partner. Omission of such a purification step enables reducing a possibility of causing RNA molecules, which are relatively unstable, to be degraded.

[Step 4]

In Step 4, the candidate RNA molecule to which the peptide receptor molecule has been bound through Step 3 is translated to produce a library of complexes (candidate RNA-peptide complexes) of the candidate RNA molecule and the candidate peptide, in each of which complexes the candidate RNA molecule and the candidate peptide encoded by the candidate RNA molecule are linked together via the peptide receptor molecule (an aspect of the "step (iii)").

The translation is preferably carried out in a cell-free translation system. Examples of the cell-free translation system include: a cell-free translation system prepared with use of an extract of wheat germ, rabbit reticulocyte, or the like; a reconstituted cell-free translation system which is prepared with use of *E. coli* ribosome by purifying and mixing factors necessary for translation; and the like (H. F. Kung, B. Redfield, B. V. Treadwell, B. Eskin, C. Spears and H. Weissbach (1977) "DNA-directed in vitrosynthesis of beta-galactosidase. Studies with purified factors" The Journal of Biological Chemistry Vol. 252, No. 19, 6889-6894; M. C. Gonza, C. Cunningham and R. M. Green (1985) "Isolation and point of action of a factor from *Escherichia coli* required to reconstruct translation" Proceeding of National Academy of Sciences of the United States of America Vol. 82, 1648-1652; M. Y. Pavlov and M. Ehrenberg (1996) "Rate of translation of natural mRNAs in an optimized in Vitrosystem" Archives of Biochemistry and Biophysics Vol. 328, No. 1, 9-16; Y. Shimizu, A. Inoue, Y. Tomari, T. Suzuki, T. Yokogawa, K. Nishikawa and T. Ueda (2001) "Cell-free translation reconstituted with purified components" Nature Biotechnology Vol. 19, No. 8, 751-755; H. Ohashi, Y. Shimizu, B. W. Ying, and T. Ueda (2007) "Efficient protein selection based on ribosome display system with purified components" Biochemical and Biophysical Research Communications Vol. 352, No. 1, 270-276). The reconstituted cell-free translation system is a system obtained by (i) dividing a cell-free translation system prepared mainly with use of an *E. coli* extract into factors and (ii) reconstituting each factor to remove a component unrelated to translation. The reconstituted cell-free translation system enables more easily preventing inhibitory substances such as nuclease and protease from being mixed in than a conventional cell-free translation system prepared with use of a cell extract. Examples of a preferable cell-free translation system include the PURE system.

It is preferable that the cell-free translation system contain substantially no nuclease (in particular, RNase). In the present specification, to "contain substantially no nuclease" means that measurement of nuclease activity shows that a numerical value indicating nuclease activity is not higher than a certain level. There are well-known methods for measuring nuclease activity. For example, degradation of a fluorescently labeled RNA substrate by RNase can be detected with reference to a change in fluorescence intensity as an index. In one example, it is preferable that the cell-free translation system contain substantially no RNase. In a case where the cell-free translation system contains substantially no nuclease (in particular, RNase), the possibility of causing RNA molecules to be degraded is reduced. This eliminates the need of performing reverse transcription reaction which is conventionally carried out after Step 4.

It is preferable that the cell-free translation system contain substantially no RNA polymerase having an activity on the candidate DNA molecule. In the present specification, an "RNA polymerase having an activity on a candidate DNA molecule" refers to an RNA polymerase capable of having a transcription reaction with respect to the candidate DNA molecule. Examples of the "RNA polymerase having an activity on a candidate DNA molecule" include an RNA polymerase that corresponds to a promoter contained in the candidate DNA and has not been deactivated. In a case where the cell-free translation system contains substantially no RNA polymerase having an activity on the candidate DNA molecule, it is unnecessary to remove, prior to Step 4, an unligated candidate DNA molecule and an unligated candidate RNA molecule.

It is preferable that the cell-free translation system contain substantially no protease. In the present specification, to "contain substantially no protease" means that measurement of protease activity shows that a numerical value indicating protease activity is not higher than a certain level. There are well-known methods for measuring protease activity. For example, degradation of fluorescently labeled casein by protease can be detected with reference to a change in fluorescence intensity as an index. In a case where the cell-free translation system contains substantially no protease, a possibility of causing a translated peptide to be degraded is reduced.

An amino acid contained in the candidate peptide may be a natural amino acid or a non-natural amino acid.

In one example of the present embodiment, a candidate RNA-peptide complex is produced in which candidate RNA-peptide complex (i) a peptide receptor molecule is linked to a C-terminus of a candidate peptide translated from the candidate RNA molecule and (ii) the candidate RNA molecule and the candidate peptide corresponding to the candidate RNA molecule are linked together via the peptide receptor molecule. In a case where the peptide receptor molecule is puromycin, the puromycin is linked to the C-terminus of a peptide chain which is elongating as a substrate of a peptide transfer reaction in a ribosome. In one example, the candidate RNA-peptide complex may have the following structure: RNA molecule-(optionally linker)-peptide receptor molecule-candidate peptide.

In a preferable example in which a cell-free translation system containing no RNase and/or protease, it is not necessary to carry out purification after Step 4.

In one example, the candidate RNA-peptide complex produced in Step 4 is not subjected to reverse transcription reaction, so that candidate RNA is single-stranded in the library of candidate RNA-peptide complexes.

[Step 5]

In Step 5, the library of candidate RNA-peptide complexes is brought into contact with a binding partner to cause a binding reaction.

The binding reaction may be based, for example, on binding between an antigen and an antibody, binding between a protein receptor and a ligand, binding between an adhesion molecule and a partner molecule, binding between an enzyme and a substrate, binding between a nucleic acid and a protein bound to the nucleic acid, binding between proteins in a signaling system, binding between a glycoprotein and a protein, binding between a sugar chain and a protein, or the like. The binding partner may be selected as appropriate depending on the purpose of selection. The binding partner may be, for example, immobilized on a solid phase or labeled by a substance captured by a solid phase. The solid phase may be any substance that can be bound to a binding partner, and is in the form of, for example, a plate, a rod, particles, beads, or the like. The solid phase may be a material insoluble in water and an organic solvent which are mediums used for screening. Examples of a material that can be used as the solid phase include plastics, glass, resins such as polystyrene, and metals such as a gold thin film. It is also possible to use magnetic beads or the like. Note that the binding partner contained in a single reaction system may be of a single kind or of two or more kinds.

A candidate RNA-peptide complex unbound to a binding partner may be removed by, for example, being washed with use of a buffer or the like.

[Step 6]

In Step 6, a reverse transcription reaction is carried out so that the candidate RNA molecule of the candidate RNA-peptide complex forms a double-stranded region with a DNA (cDNA) molecule. In the present embodiment, the reverse transcription reaction may be carried out after the candidate RNA-peptide complex is dissociated from the binding partner by elution or the like, or may be carried out while being bound to the binding partner. Performing the reverse transcription reaction in a state where the candidate RNA-peptide complex is bound to the binding partner advantageously reduces cDNA bound via RNA (aptamer). The reverse transcription reaction can be conducted, for example, by an ordinary method. In the present embodiment, the reverse transcription reaction is carried out after Step 5. This advantageously eliminates the need to carry out purification for the reverse transcription reaction prior to Step 5. Accordingly, the present embodiment is free from a problem of the conventional method that purification reduces diversity of candidate RNA molecules.

[Step 7]

In Step 7, each candidate RNA-peptide complex is dissociated from the binding partner and recovered. A method for dissociation may be selected as appropriate depending on the type of binding with the binding partner. For example, a protease such as ficin, papain, or trypsin, or an antibody sequence-specific protease such as IdeS or IdeZ can be used. By conducting Steps 5 through 7, a desired RNA-peptide complex is selected from the library of candidate RNA-peptide complexes (an aspect of the "step (iv)").

[Step 8]

The RNA-peptide complexes which have been selected may be then subjected to analysis of an RNA sequence and/or a peptide sequence, and the like. The analysis may be performed by use of an ordinary amino acid sequencer, or by performing reverse transcription of a DNA from the RNA bound to the peptide and analyzing a base sequence of a cDNA thus obtained. Further, purification and quantification may be carried out as appropriate.

Further, the above-described Step 1 may be carried out using the cDNA obtained through this step. For example, the cDNA obtained through this step or an amplification product thereof is subjected to a PCR reaction with use of a Reverse primer in which at least one nucleoside at a 5' end thereof is substituted by a 2'-modified nucleoside derivative and an ordinary Forward primer. Then, DNA molecules obtained by the PCR reaction are used to carry out Steps 2 through 7 again. Thus repeating a cycle consisting of Steps 1 through 7 a plurality of times enables enrichment of a candidate RNA-peptide complex having desired properties. This candidate RNA-peptide complex is then subjected to analysis.

Method in Accordance with Another Embodiment

In a method in accordance with another embodiment, the order of performing Step 5 and Step 6 in the above-described embodiment may be reversed. That is, in Step 4 of the conventional mRNA display method, the candidate RNA molecule to which the peptide receptor molecule has been bound through Step 3 is translated, and then a reverse transcription reaction corresponding to Step 6 is carried out so that the candidate RNA molecule of the candidate RNA-peptide complex forms a double-stranded region with a DNA (cDNA) molecule. Then, a binding reaction (corresponding to Step 5) in which the library of candidate RNA-peptide complexes is brought into contact with a binding partner is carried out.

In the reverse transcription reaction, adding EDTA to a sample and then subjecting the sample to a heating treatment enables increasing an efficiency of the reverse transcription reaction.

Example Applications

The above-described embodiments are applicable, for example, to: identification of a protein which interacts with a drug discovery target molecule; analysis of a drug discovery target protein; acquisition and modification of an antibody molecule; identification of an antigen protein recognized by an antibody and an antigen site of the antigen protein; modification of various functional proteins and peptides; confirmation of activity of a vaccine; and the like.

In particular, in the above-described embodiments, which are obtained by improving mRNA display method which is one of peptide selection methods, 5' ends of antisense strands of a DNA library are modified by 2'-O-methylguanosine to reduce occurrence of addition of one or several bases and thus allow an mRNA library to have uniform 3' ends. This enables a dramatic increase (from approximately 50% to approximately 90%) in efficiency of linking of the 3' ends of the mRNA library to a peptide receptor molecule (e.g., puromycin). Further, exclusion of RNA polymerase from a cell-free translation system (PURE system) eliminates the need to cause template DNA and mRNA containing no puromycin to be removed by purification, nuclease treatment, or the like prior to translation. Further, use of the PURE system which does not include RNase allows RNA to be relatively stable, and thus eliminates the need to carry out purification and a reverse transcription reaction immediately after translation. These enable purification and reverse transcription to be carried out during positive selection, and thus simplify peptide selection. This enables high-throughput peptide screening which employs a multi-channel automatic dispenser. Further, since the number of overall steps is small and RNA degradation and adsorption can be reduced during operation, it becomes possible to carry out peptide screening with increased efficiency. Further, carrying out operations in parallel enables cost reduction.

As a result, it becomes possible to achieve: discovery of new drug discovery targets by screening of antibody drugs and identification of causes of diseases whose causes have been unidentified; support of development of highly effective vaccines enabled by quantification of effective antibody production by vaccines; assessment of a state of health by immunoassay; classification of diseases; and the like. It also becomes possible to help promote research on rare diseases. Thus, the methods in accordance with the above-described embodiments are applicable to various purposes.

Examples of Specific Aspects in Accordance with the Present Invention (1) A method for producing a complex of an RNA molecule encoding a peptide and the peptide encoded by the RNA molecule, the method including the steps of: (i) producing the RNA molecule from a DNA molecule via transcription, the DNA molecule (a) containing a promoter region and a region that is located downstream of the promoter region and encodes the peptide and (b) containing at least one 2'-modified nucleoside derivative on a 5' end side of an antisense strand that is located most downstream; (ii) binding, to a 3' end of the RNA molecule obtained in the step (i), a peptide receptor molecule with use of a splint polynucleotide as an anchorage; and (iii) performing translation of the RNA molecule, to which the peptide receptor molecule has been bound through the step (ii), to produce the complex in which the receptor molecule and the peptide encoded by the RNA molecule are linked via the peptide receptor molecule.

(2) The method as set forth in (1), wherein the translation is performed in an in vitro translation system containing substantially no RNase.

(3) The method as set forth in (1) or (2), wherein the translation is performed in an in vitro translation system containing substantially no RNA polymerase having an activity on the DNA molecule.

(4) The method as set forth in any one of (1) through (3), wherein the DNA molecule contains two consecutive 2'-modified nucleoside derivatives.

(5) The method as set forth in any one of (1) through (4), wherein the at least one 2'-modified nucleoside derivative is 2'-O-methylguanosine.

(6) The method as set forth in any one of (1) through (5), wherein the peptide receptor molecule is puromycin.

(7) The method as set forth in any one of (1) through (6), wherein a plurality of different complexes of an RNA molecule and a peptide, each of the plurality of different complexes being the complex, are produced with use of a plurality of respective different DNA molecules, each of which is the DNA molecule.

(8) An mRNA display method including a method recited in any one of (1) through (7), the mRNA display method further including the step of: (iv) selecting a desired complex from among the complex of the RNA molecule and the peptide obtained in the step (iii). Note that prior to the step (iv), a least part of the RNA molecule of the complex of the RNA molecule and the peptide may form a double-stranded structure with a complementary cDNA (DNA) molecule.

(9) The method as set forth in (8), wherein a cycle consisting of the steps (i) through (iv) is repeated a plurality of times.

(10) A DNA library for use in an mRNA display method, containing: a plurality of different candidate DNA molecules, each of the plurality of different candidate DNA molecules (i) containing a promoter region and a region that is located downstream of the promoter region and encodes a candidate peptide and (ii) containing at least one 2'-modified nucleoside derivative on a 5' end side of an antisense strand that is located most downstream.

(11) The DNA library as set forth in (10), containing $10^{13}$ or more different candidate DNA molecules.

The following will provide Examples to more specifically describe embodiments of the present invention. As a matter of course, the present invention is not limited to Examples provided below, and details of the present invention can be realized in various manners. Further, the present invention is not limited to the embodiments described above, and it may be varied in various ways within the scope of the appended claims. Thus, an embodiment based on a combination of technical means disclosed in different embodiments is encompassed in the technical scope of the present invention. Furthermore, all of the publications and patents cited in the present specification are incorporated herein by reference in their entirety. This application claims priority on Japanese Patent Application, Tokugan, No. 2017-053621 filed in

EXAMPLES

Example 1: Search for Antigen Peptide from Serum of Autoimmune Encephalomyelitis (EAE) Model Laboratory Mouse

[Method]

(1) Production of Autoimmune Encephalomyelitis (EAE) Laboratory Mouse Antibody-Immobilized Magnetic Beads A C57B6 mouse (10-week old) was immunized with MOG35-55 peptide (MEVGWYRSPFSRVVHLYRNGK) (SEQ ID NO: 1) with use of Freund's complete adjuvant. 20 to 22 days after the immunization, whole blood was recovered and mixed with an equal amount of PBS. A serum component was separated using Ficoll. 100 µL of the serum was bound to 100 µL of Protein G magnetic beads (dynabeads) at 4° C. for 1 hour. A resultant product was washed with 500 µL of washing buffer (50 mM Tris-HCl, pH 7.5, 300 mM NaCl, 0.1% Triton X-100) for 5 times to produce magnetic beads on which an EAE mouse antibody was immobilized.

(2) Production of Library DNA 10 nM random library DNA: GCTGCCGCTGCCGCTGCC (MNN)n CATATGTATATCTCCTTCTTAAAG (n=8) (SEQ ID NO. 2) or cDNA (from the second cycle) recovered in (7) below was subjected to PCR (94° C.: 10 seconds, 58° C.: 10 seconds, 72° C.: 30 seconds, 8 cycles) with use of 1 µM F-primer (CCTAATACGACTCACTATAGGGTTAACTT-TAAGAAGGAGATATACATATG) (SEQ ID NO. 3) and 1 µM R-primer (GmGmTCGGCGGAT-CAAAGTAGCTGCCGCTGCCGCTGCCGCA (Gm: 2'-O-methylguanosine)) (SEQ ID NO: 4). Thus produced was a template DNA library: CCTAATACGACTCAC-TATAGGGTTAACTTTAAGAAGGAGATATACATATG (NNK)n TGCGGCAGCGGCAGCGGCAGCTACTTT-GATCCGCCGACC (n=8) (SEQ ID NO. 5) containing a T7 promoter sequence, a Shine-Dalgarno sequence (SD sequence), and the random ORF region. The template DNA library was purified using FastGene Gel/PCR Extraction Kit.

(3) Transcription Reaction

From 10 nM template DNA library, an RNA library was produced by carrying out transcription at 37° C. for 1 hour in a 50 µL scale (0.086 ng of T7 RNA polymeras, 4.5 mM NTP, mM HEPES-KOH (pH 7.6), 20 mM MgCl₂, 2 mM spermidine, 5 mM DTT).

(4) Addition of Puromycin (Pu)

To 3 µL of the RNA library obtained, 1 µL of 10 mM ATP, 2 µL of 100 µM Pu-DNA (CTCCCGCCCCCGTCC [spacer18]₅CC[Puromycin]) (SEQ ID NO: 6), 2 µL of 100 µM splint-DNA (GGGCGGGAGGGTCGGCGGATCAA) (SEQ ID NO: 7), and 13 µL of ×1 T4 DNA ligase buffer were added. A mixture thus obtained was heated at 95° C. for 3 minutes. The mixture was cooled at room temperature. Then, 0.5 µL of T4 DNA Ligase (70 U/µL) was added, and a reaction was allowed to take place at 37° C. for 1.5 hours.

(5) Translation Reaction/Production of mRNA-Peptide Library 2.4 µL of the resultant puromycin-added RNA library was caused to react using a PURE system in a 20 µL-scale (14 µL of Solution A, 2 µL of Solution B (RNA polymerase, RF1 minus), 2 µL of 50 mM Hepes-KOH (pH 7.6), 100 mM KCl, 10 mM MgCl₂, 30% glycerol) at 37° C. for 1 hour. Then, 30 µL of binding buffer (50 mM Tris-HCl (pH 8.0), 61 mM EDTA) was added.

(6) Peptide Selection

The mRNA-peptide library obtained in (5) was added to 10 µL of Protein G magnetic beads (dynabeads) on which an antibody derived from a healthy mouse was immobilized, and a reaction was allowed to take place at 4° C. for 30 minutes. The supernatant was added to 10 µL of magnetic beads to which an antibody derived from an EAE mouse was bound, and a reaction was allowed to take place at 4° C. for 30 minutes. The magnetic beads were washed with 50 µL of washing buffer (50 mM Tris-HCl pH7.5, 300 mM NaCl, 0.1% Triton X-100) for 8 times.

(7) Reverse Transcription Reaction

To the magnetic beads, 1× ProtoScript buffer containing 200 µM dNTP, 1 mM DTT, 0.5 µL of 200 nM Primer P2 (GGTCGGCGGAT-CAAAGTAGCTGCCGCTGCCGCTGCCGCA) (SEQ ID NO: 8), and 200 U of ProtoScriptII RTase was added, and a reaction was allowed to take place at 37° C. for 30 minutes. The supernatant was discarded, and the remainder was washed once using 50 µL of washing buffer.

(8) Elution

50 µL of elution buffer (10 mM Tris-HCl (pH 8.0), 75 mM KCl, 0.1% Triton X-100, 10 mM DTT) was added. A mixture thus obtained was heated at 97° C. for 3 minutes, and the supernatant was recovered.

Five cycles of the above steps (3) through (8) were carried out using biomek FX. PCR was conducted using Primer-F2: CCGAAGGAGATATACATATG (SEQ ID NO: 9) and Primer-R2: ANNCTGCCGCTGCCGCTGC (N=A,G,C,T) (SEQ ID NO: 10). Single-read sequencing (80 bases) was carried out using HiSeq 2500.

[Results]

Figure 2:
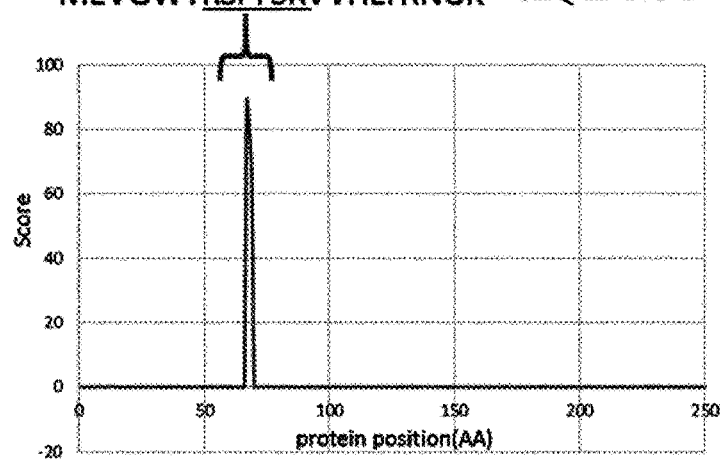
FIG. 2 is a view illustrating results in Example 1.
Figure 2:
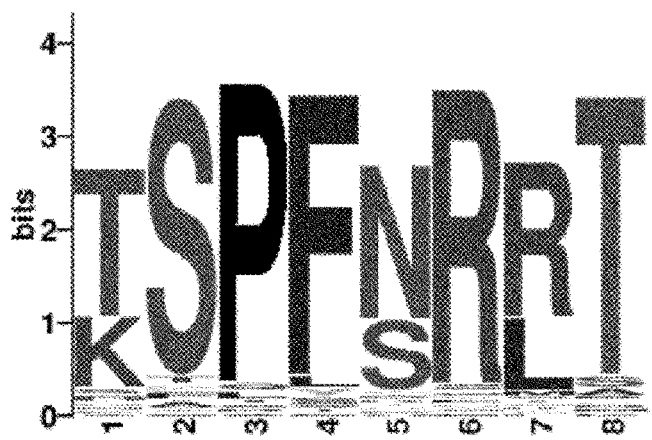

The results are shown in FIG. 2. (A) of FIG. 2 illustrates peptide sequences obtained from the peptide selection and scores of the peptide sequences with respect to MOG protein. The seventh position of Rank 2 is a stop codon. It is thus presumed that only the sequence of the first to sixth positions was translated. (B) of FIG. 2 illustrates a MOG protein recognition site of the EAE mouse antibody. (C) of FIG. 2 illustrates a sequence motif of the EAE mouse antibody with respect to an antigen. As indicated by FIG. 2, a sequence motif having a high homology with part of the MOG35-55 peptide was obtained from the amino acid sequences obtained. Further, the search detected no sequences corresponding to other sites of the MOG protein, and thus succeeded in specifically obtaining a peptide which caused the disease.

Example 2: Improvement of Efficiency of Peptide Selection by 2'-O-Methylguanosine (1) Production of DNA Produced was 10 nM template DNA in which guanosine (WT) or 2'-O-methylguanosine (Gm) had been introduced to two bases at a 5' end of an antisense strand of FLAG peptide template double-bonded DNA:

(SEQ ID NO: 11)
GGCGTAATACGACTCACTATAGGGTTAACTTTAACAAGGAGAAA

AACATGAAGTACTCCCCAACCGACTGCGGCAGCGGCAGCGGCAG

CTACTTTGATCCGCCGACC.

(2) Transcription Reaction

Each template DNA (10 nM) was caused to react in a 20 μL scale (0.086 ng of T7 RNA polymerase, 4.5 mM NTP, 40 mM HEPES-KOH (pH 7.6), 20 mM MgCl$_2$, 2 mM spermidine, 5 mM DTT) at 37° C. for 1 hour, and mRNA thus transcribed was quantified using Qubit.

(3) Peptide Selection

Each mRNA (1 μM) and anti-FLAG (registered trademark) M2 antibody magnetic beads (Sigma M8823) serving as a solid phase carrier were used to conduct selection using Biomek FX in a similar manner to Example 1. Each cDNA obtained was quantified by qPCR.

[Results]

Figure 3:
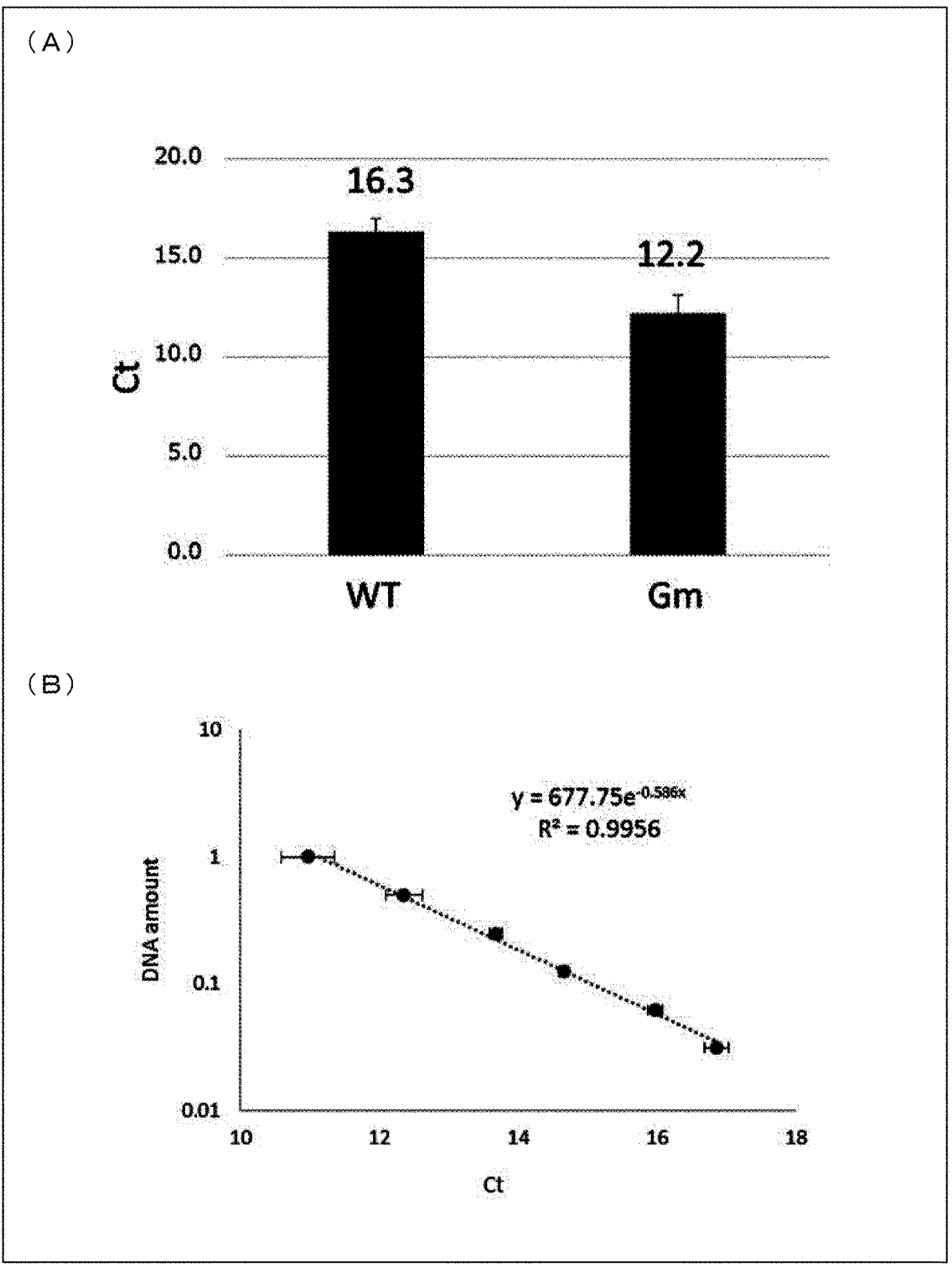
FIG. 3 is a view illustrating results in Example 2.

The results are shown in FIG. 3. (A) of FIG. 3 illustrates efficiencies of peptide recovery achieved with use of respective template DNAs. (B) of FIG. 3 illustrates a calibration curve of cDNA obtained by qPCR. As calculated from FIG. 3, it was found that the use of the template DNA into which 2'-O-methylguanosine (Gm) had been introduced improved the efficiency of peptide selection by approximately 10 times.

Example 3: Comparison with Conventional Method

Double-stranded DNAs encoding respective three types of FLAG peptides were produced. The double-stranded DNAs differed from one another only in terms of a sequence (underlined) located downstream of a stop codon and used for linkage with Pu-DNA. Efficiencies of peptide selection carried out with use of the respective double-stranded DNAs were examined.

TABLE 1

| | Sequence |
|---|---|
| Template DNA 1 | CCTAATACGACTCACTATAGGGTTAACTTTAAG AAGGAGATATACATATGAAGTACTCCCCAACCG ACTGCAAGAAGGACTACAAGGACGACGACGACA AGTGCGGCAGCGGCAGCGGCAGCTAGGACGGGG GGCGGAAA |
| Template DNA 2 | CCTAATACGACTCACTATAGGGTTAACTTTAAG AAGGAGATATACATATGAAGTACTCCCCAACCG ACTGCAAGAAGGACTACAAGGACGACGACGACA AGTGCGGCAGCGGCAGCGGCAGCTACTTTGATC CGCCGACC |
| Template DNA 3 | CCTAATACGACTCACTATAGGGTTAACTTTAAG AAGGAGATATACATATGAAGTACTCCCCAACCG ACTGCAAGAAGGACTACAAGGACGACGACGACA AGTGCGGCAGCGGCAGCGGCAGCTACTTTGATC CGCCGAC*C* (C*: 2'-O-methylguanosine is introduced into an antisense strand) |

Template DNA 1=SEQ ID NO: 12

Template DNA 2 and Template DNA 3=SEQ ID NO: 13

Experiment 1: Examination of Efficiency of mRNA/Pu-DNA Ligation

From the above template DNAs, mRNAs were produced using T7 RNA polymerase. For each mRNA, quantification of RNA was carried out using Qubit (registered trademark) RNA HS Assay Kit, and 7 μM of RNA was prepared. RNA derived from Template DNA 1 was mixed with 15 μL of ×0.6 T4 RNA Ligase buffer (attached) containing 10 μM Pu-DNA (CTCCCGCCCCCCGTCC[spacer18]$_5$CC[Puromycin]) (SEQ ID. NO. 6) and 1 mM ATP, and the mixture was heated at 95° C. for 2 minutes and cooled at room temperature. Then, 1 μL (10 U) of T4 RNA Ligase 1 (manufactured by NEB) was added, and a reaction was allowed to take place at 37° C. for 1.5 hours. RNA (3 μL) derived from Template DNA 2 and RNA (3 μL) derived from Template DNA 3 were each mixed with 15 μL of ×0.6 T4 DNA Ligase buffer (attached, containing 1 mM ATP) containing 5 μM Pu-DNA and 5 μM splint-DNA (GGGCGGGAGGGTCGGCGGAT-CAA), (SEQ ID. NO. 7) and the mixture was heated at 95° C. for 2 minutes and then cooled at room temperature. Then, 1 μL (400 U) of T4 DNA Ligase (manufactured by NEB) was added, and a reaction was allowed to take place at 37° C. for 1.5 hours or at 16° C. overnight (16 hours). 0.5 μL of each product thus obtained was subjected to electrophoresis (180 V, 45 min) with use of 7M urea 10% PAGE. An mRNA/Pu-DNA linking site had a structure illustrated in (A) of FIG. 4.

Figure 4:
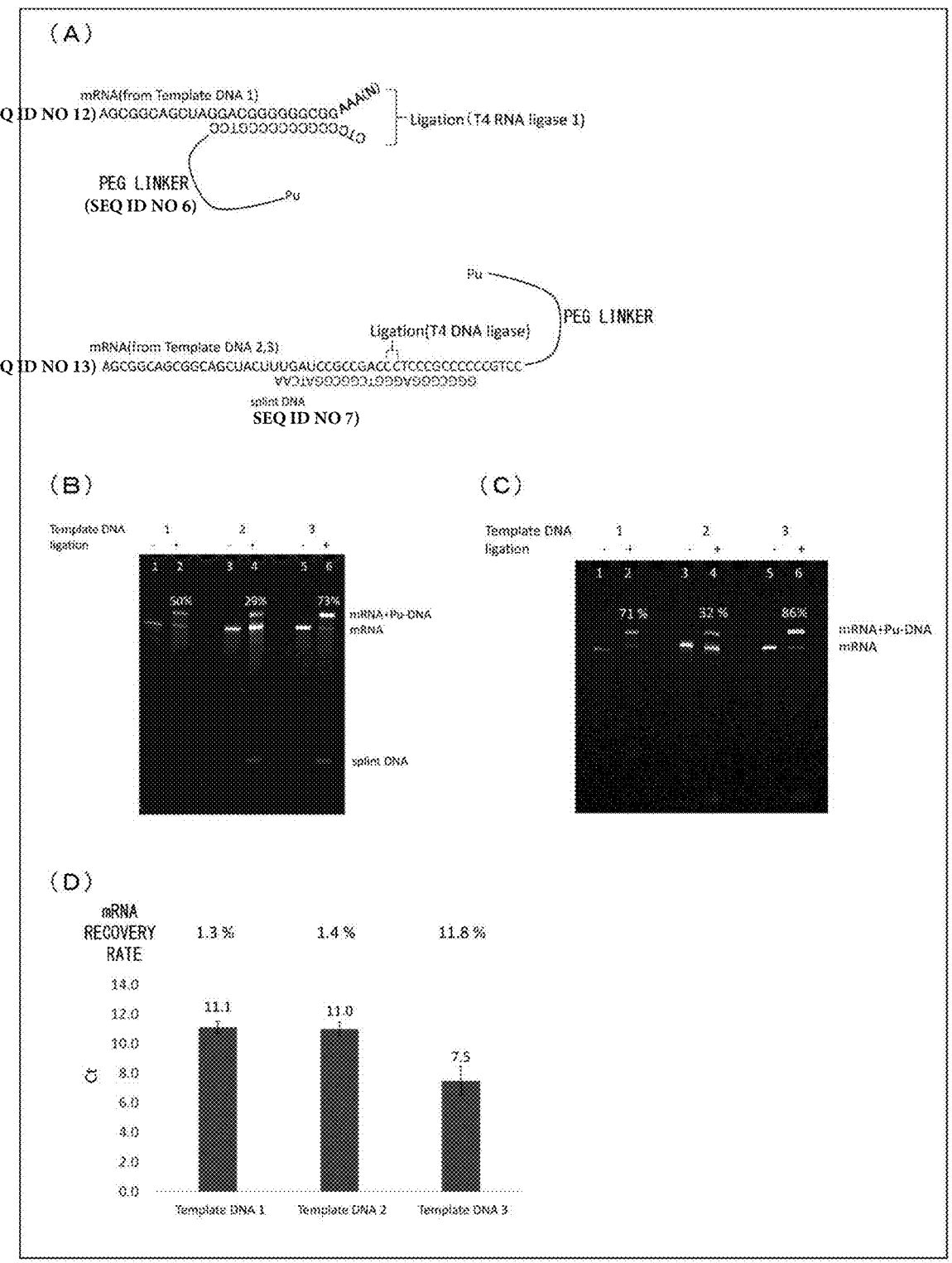
FIG. 4 is a view illustrating results in Example 3.

The results are shown in (B) and (C) of FIG. 4. (B) of FIG. 4 illustrates efficiencies of mRNA/Pu-DNA ligation achieved in cases where the reaction was conducted at 37° C. for 1.5 hours. (C) of FIG. 4 illustrates efficiencies of mRNA/Pu-DNA ligation achieved in cases where the reaction was conducted at 16° C. overnight. As illustrated in (B) and (C) of FIG. 4, under both conditions, the efficiency of mRNA/Pu-DNA ligation was in a descending order of: Template DNA 3>Template DNA 1>Template DNA 2. It was thus revealed that the template DNA employing Gm exhibited the highest efficiency. The higher efficiency of Template DNA 3 than that of Template DNA 1 suggested a possibility that a decrease in efficiency is caused by the fact that puromycin is located on an inner side, rather than on an end side, of the molecule when a hairpin structure is formed in the case of Template 1.

Experiment 2: Examination of Efficiency of Peptide Recovery

Each mRNA (7 μM) used in Experiment 1 and 10 μL of anti-FLAG (registered trademark) M2 antibody magnetic beads (sigma M8823) serving as a solid phase carrier were used to conduct selection using Biomek FX in a similar manner to Example 2. Each cDNA thus obtained was quantified by qPCR. For peptide selection using Template DNA 1, T4 RNA ligase 1 (manufactured by NEB) was used.

The results are shown in (D) of FIG. 4. (D) of FIG. 4 illustrates efficiencies of peptide selection achieved with use of respective template DNAs. The template DNA employing Gm (Template DNA 3) exhibited the highest peptide recovery rate. It was thus revealed that it was far more efficient to conduct mRNA/Pu-DNA ligation by use of Gm than to conduct mRNA/Pu-DNA ligation by forming a hairpin structure (Template DNA 1) on a run-off (a base added to an end) product of RNA polymerase. Template DNAs 1 through 3 exhibited an mRNA collection rate of 1.3%, 1.4%, and 11.8%, respectively.

Example 4: Method of Collecting Peptide with Use of Protease

[Method]

Under the same conditions as Example 2, FLAG peptide-cDNA was prepared, and a method for collecting cDNA from anti-FLAG (registered trademark) M2 antibody magnetic beads (sigma M8823) was studied.

Figure 5:
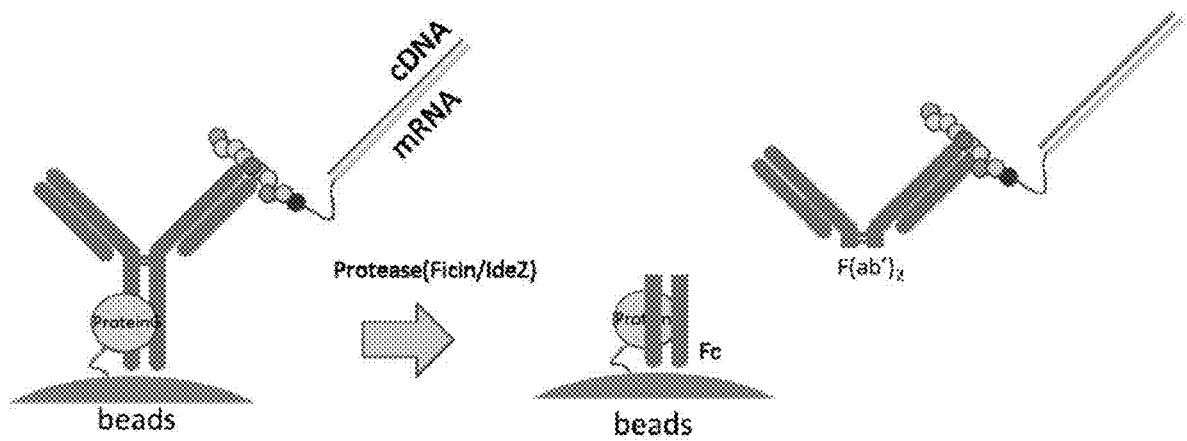
FIG. 5 is a view illustrating a method for eluting cDNA with use of protease in Example 4.

To the magnetic beads, 10 μL of ficin buffer (50 mM Tris-HCl (pH 6.8), 10 mM EDTA, 5 mM cystein) and 0.1 mg to 2 mg of ficin (SIGMA: F4125) was added, and a mixture thus obtained was left to stand at 37° C. for 1 hour. The supernatant was heated at 98° C. for 5 minutes to deactivate ficin, and cDNA eluted was quantified by qPCR. Further, cDNA that was remaining on the beads was collected by being heated in ficin buffer at 98° C. for 5 minutes, and was quantified by qPCR. FIG. 5 is a view illustrating a method for eluting cDNA with use of protease in Example 4.

Figure 6:
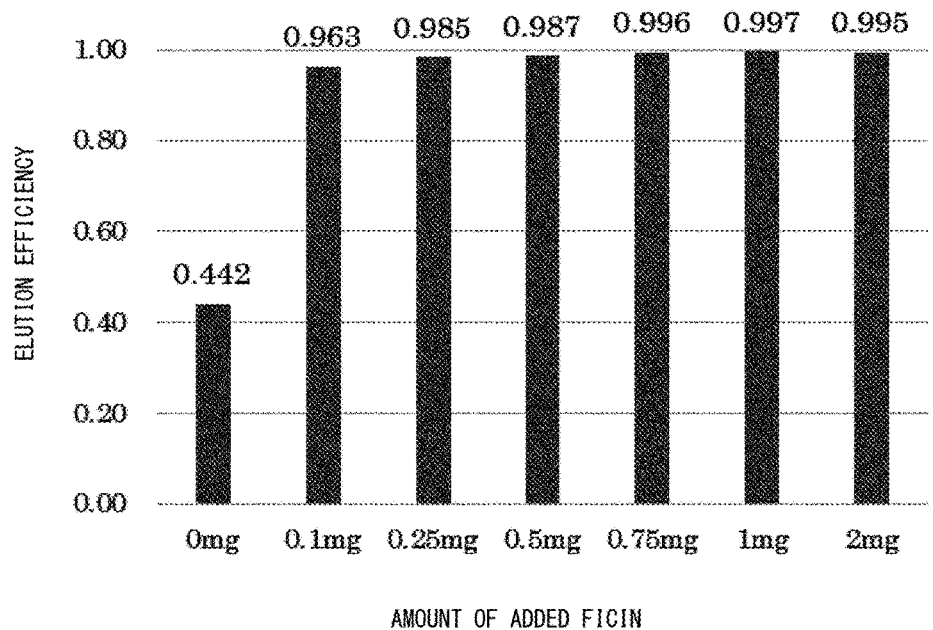
FIG. 6 is a view illustrating results in Example 4.

The results are shown in FIG. 6. As indicated by FIG. 6, it was found that using ficin in an amount of 0.1 mg or more enabled eluting 95% or more of the entire cDNA, and using Ficin in an amount of 0.75 mg or more enabled eluting 99% or more of the entire cDNA. It is possible to similarly use a protease such as papain or trypsin, or an antibody sequence-specific protease such as IdeS or IdeZ.

Example 5: Another Example of DECODE

[Method]
With use of the same template DNA used in Example 2, a FLAG peptide-mRNA complex was produced in a 20 µL scale. The FLAG peptide-mRNA complex was divided into four equal amounts. 0.23 µL of EDTA (0.5 M) was added to three samples among four samples thus obtained. The three samples were left to stand still at 25° C. for 10 minutes, at 50° C. for 10 minutes, and at 95° C. for 1 minute, respectively. 0.33 µL of MgCl$_2$ (0.5 M) was added, and 20 µL of reverse transcription mix (lx ProtoScript buffer containing 1 mM dNTP, 10 mM DTT, 0.125 µL of 0.2 µM Primer P2 (GGTCGGCGGAT-CAAAGTAGCTGCCGCTGCCGCTGCCGCA) (SEQ ID. NO. 80, and 100µ of ProtoScriptII RTase) was added. A reaction was allowed to take place at 37° C. for 40 minutes. A resultant product was subjected to a binding reaction in which the resultant product was bound to 1 µL of anti-FLAG M2 antibody magnetic beads (SIGMA: M8823) at room temperature for 30 minutes. Then, a resultant product was washed using 50 µL of washing buffer for 10 times. 30 µL of elution buffer (10 mM Tris-HCl (pH 8.0), 75 mM KCl, 0.1% Triton X-100, 10 mM DTT) was added, and a mixture thus obtained was heated at 97° C. for 3 minutes. The supernatant was recovered immediately after the heating and was quantified by qPCR. To the remaining one sample, 20 µL of binding buffer (50 mM Tris-HCl (pH 8.0), 61 mM EDTA) was added. A mixture thus obtained was subjected to a binding reaction in which the mixture was bound to 1 µL of anti-FLAG M2 antibody magnetic beads (SIGMA: M8823) at room temperature for 30 minutes. Then, a resultant product was washed using 50 µL of washing buffer for 10 times. 30 µL of elution buffer (10 mM Tris-HCl (pH 8.0), 75 mM KCl, 0.1% Triton X-100, 10 mM DTT) was added, and a mixture thus obtained was heated at 97° C. for 3 minutes. The supernatant was immediately recovered after the heating and was quantified by qPCR (control).

Figure 7:
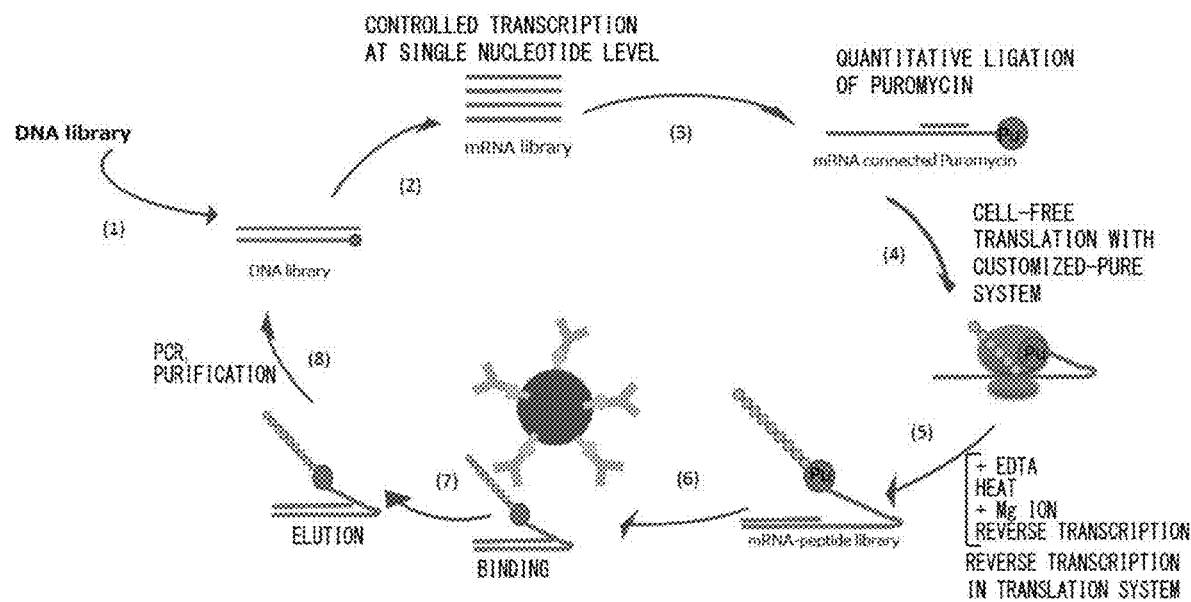
FIG. 7 is a view illustrating another example method of the present invention.

The DECODE conducted in Example 5 is illustrated in FIG. 7.

Figure 8:
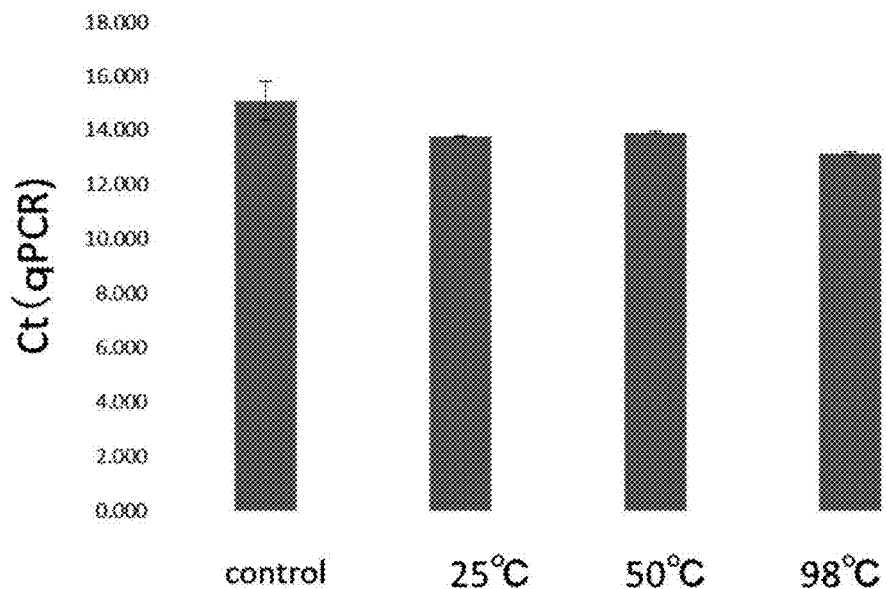
FIG. 8 is a view illustrating results in Example 5.

[Results]
The results are shown in FIG. 8. As indicated by FIG. 8, it is possible to conduct the DECODE by a procedure in which cDNA synthesis is carried out immediately after translation and then an antibody-binding reaction is carried out. By conducing high-temperature treatment after addition of EDTA, it is possible to expect a slight improvement in efficiency.

INDUSTRIAL APPLICABILITY

The present invention is applicable, for example, to the field of discovery of drugs such as molecularly-targeted drugs typified by antibody drugs.

The invention claimed is:

1. A method for producing a complex of an RNA molecule encoding a peptide and the peptide encoded by the RNA molecule,
said method comprising the steps of:
(i) producing the RNA molecule from a DNA molecule via transcription, the DNA molecule comprising a sense strand, an antisense strand, a promoter region and a region that is located downstream of the promoter region and encodes the peptide where the antisense strand provides a template for transcription of the region encoding the peptide and comprises at least one 2'-modified nucleoside derivative at the last position of the 5' end of the antisense strand,
(ii) binding, to a 3' end of the RNA molecule obtained in step (i), a peptide receptor molecule with use of a splint polynucleotide as an anchorage; and
(iii) performing, in an in vitro translation system containing no RNA polymerase having an activity on the DNA molecule, translation of the RNA molecule, to which the peptide receptor molecule has been bound through step (ii), to produce the complex in which the RNA molecule and the peptide encoded by the RNA molecule are linked via the peptide receptor molecule, wherein
purification of the RNA molecule obtained in step (i) is not carried out prior to step (ii) and purification of the RNA molecule obtained through step (ii) to which the peptide receptor molecule has been bound is not carried out prior to step (iii).

2. The method as set forth in claim 1, wherein the at least one 2'-modified nucleotide derivative comprises two consecutive 2'-modified nucleoside derivatives.

3. The method as set forth in claim 1, wherein the at least one 2'-modified nucleoside derivative is 2'-O-methylguanosine.

4. The method as set forth in claim 1, wherein the peptide receptor molecule is puromycin.

5. The method as set forth in claim 1, wherein a plurality of different complexes of an RNA molecule and a peptide are produced with use of a plurality of respective different DNA molecules, each of which is a DNA molecule of step (i).

6. An mRNA display method comprising the method recited in claim 1,
the mRNA display method further comprising the step of:
(iv) selecting a desired complex from among complexes of the RNA molecule and the peptide obtained in step (iii).

7. The mRNA display method as set forth in claim 6, wherein a cycle consisting of steps (i) through (iv), and further comprising (v) obtaining, by performing a reverse transcription reaction using the complex selected in step (iv), a DNA molecule containing the region that encodes the peptide, and (vi) obtaining, by amplifying the DNA molecule obtained in step (v) by PCR, the DNA molecule that is subject to the transcription in step (i) and contains the promoter region and the region that is located downstream of the promoter region and encodes the peptide, is repeated a plurality of times.

8. The mRNA display method as set forth in claim 7, wherein
the in vitro translation system contains no RNase, and
purification of the complexes of the RNA molecule and the peptide obtained in step (iii) is not carried out prior to step (iv).

* * * * *